United States Patent [19]

Tracy et al.

[11] Patent Number: 4,885,158

[45] Date of Patent: Dec. 5, 1989

[54] HEAT STABLE QUATERNIZED LACTAMS HAVING OXYLATED SULFUR ANIONS

[75] Inventors: David J. Tracy, Lincoln Park; Thomas Rizzo, Bloomfield; Robert B. Login, Oakland, all of N.J.

[73] Assignee: GAF Corporation, Wayne, N.J.

[21] Appl. No.: 188,522

[22] Filed: Apr. 29, 1988

[51] Int. Cl.$^4$ .............. A61K 7/075; D06M 13/40; C07D 223/10
[52] U.S. Cl. ........................................ 424/69; 424/62; 424/63; 424/64; 424/70; 424/71; 424/72; 514/183; 514/212; 514/327; 514/424; 252/8.75; 252/8.8; 540/451; 540/531; 546/243; 548/546; 548/550
[58] Field of Search ............... 540/531, 451; 546/243; 548/546, 580; 252/8.75, 8.8; 514/212, 183, 327, 424; 424/62, 63, 64, 69, 70, 71, 72

[56] References Cited

U.S. PATENT DOCUMENTS 4,732,990 3/1988 Login et al. .................... 540/531

*Primary Examiner*—Robert T. Bond
*Attorney, Agent, or Firm*—Marilyn J. Maue; Joshua J. Ward

[57] ABSTRACT

The invention relates primarily to quaternized compounds having the formula

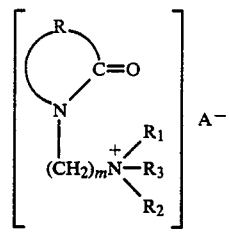

wherein m is an integer having a value of from 1 to 4; R is alkylene having from 3 to 8 carbon atoms and is optionally substituted with $C_1$ to $C_4$ alkyl; $R_1$, $R_2$ and $R_3$ are each independently selected from the group of alkyl, alkyloxyalkyl, alkyloxyalkenyl, hydroxyalkyl, aryl, aralkyl, alkaryl, alkyl amidoalkyl, alkyl carbamoylalkyl, aryl amido alkyl and aryl carbamoyalkyl radicals, and $R_2$ and $R_3$, together with the quaternized nitrogen atom can form a heterocyclic radical containing from 1 to 2 heteroatoms selected from the group of nitrogen, sulfur and oxygen, in which case $R_1$ can represent a double bond in the heterocyclic structure or can be any of the aforementioned groups for $R_1$, $R_2$ and $R_3$; said groups $R_1$, $R_2$ and $R_3$ each having from 1 to 30 carbon atoms and at least one of $R_1$, $R_2$ and $R_3$ is a radical having from 8 to 30 carbon atoms when $R_2$ and $R_3$ are not part of a heterocyclic moiety; and $A^-$ is an anion derived from an oxylated sulfur compound, having the formula:

$R'SO_3^-$ wherein $R'$ is alkyl, alkoxy, phenyl, phenoxy, alkylphenyl, alkylphenoxy, phenylalkyl or phenoxyalkyl and wherein the alkyl moieties of said $R'$ groups contain from 1 to 20 carbon atoms and said $R'$ groups are optionally alkoxylated with from 1 to 20 units of ethyleneoxide and/or propylene oxide. The invention also relates to the preparation and use of said quaternized compounds.

20 Claims, No Drawings

HEAT STABLE QUATERNIZED LACTAMS HAVING OXYLATED SULFUR ANIONS

BACKGROUND OF THE INVENTION

The selection of components for hair and skin treating formulations presents numerous difficulties involving compatibility. Several hair treatment and shampoo formulations have been developed which aim to provide conditioning action during cleansing so as to leave the hair soft, manageable and lustrous and thus to eliminate a separate application of cream rinses or conditioning treatments. Problems arise from the limited compatibility of anionic detergents with commercial cationic conditioning agents which precipitate out of solution in shampoo formulations.

Shampoo formulations have employed conventional anionic surfactants such as sodium lauryl sulfate, ammonium lauryl sulfate, ethanol amine lauryl sulfates and sodium lauryl ether sulfates which have been found to be incompatible with most cationic conditioning agents at effective concentration levels.

Additionally, reproducible thickening for formulations containing anionic detergents such as sodium α-olefin sulfonates is very difficult to achieve.

Another problem encountered in hair conditioning shampoos is one of a preservative nature. It has been found that shampoos, containing inadequate preservative, on standing develop strands of pseudomonas aerouginosa which are clearly visible in the liquid and which may cause scalp infection. Consequently, separate biocidal agents are added to the formulation to prevent development of this bacteria and prevent skin infection. These and many other problems are encountered in the formulation of various shampoos, conditioners and cream rinses. Certain of these difficulties are also encountered in skin lotions, healing salves, mouthwashes, etc.

Still another problem is one of heat stability at temperatures customarily encountered during storage. Certain quaternized lactam halides have been developed to build viscosity and to impart hair and skin conditioning properties in cosmetic formulations. While these compounds possess all of the above benefits, as well as being highly compatible with anionic components of cosmetic formulations and providing preservative properties in shampoos, hair and skin creams and lotions, they are not particularly stable over long periods of storage at high temperatures, e.g. at temperatures in excess of 100° F.

Accordingly it is an object of this invention to minimize or obviate the above problems while providing additional benefits in hair and skin treating formulations.

Another object of the invention is to provide novel quaternized nitrogen containing compounds having unique properties and excellent heat stability.

Another object is to provide novel quaternized nitrogen containing compounds having excellent hair conditioning and thickening properties when incorporated into a shampoo and having high compatibility with components of hair and skin treating formulations.

Another object is to provide an economical and commercially feasible method for the preparation of said novel quaternized nitrogen containing compounds.

Still another object is to provide processes for the use of said quaternized compounds.

These and other objects will become apparent from the following description and disclosure.

THE INVENTION

In accordance with this invention, there is provided quaternized compounds having the formula

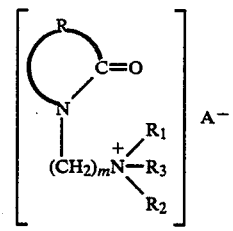

wherein m is an integer having a value of from 1 to 4; R is alkylene having from 3 to 8 carbon atoms and is optionally substituted with $C_1$ to $C_4$ alkyl; $R_1$, $R_2$ and $R_3$ are each independently selected from the group of alkyl, alkyloxyalkyl, alkyloxyalkenyl, hydroxyalkyl, aryl, aralkyl, alkaryl, alkyl amidoalkyl, alkyl carbamoylalkyl, aryl amido alkyl and aryl carbamoylalkyl radicals, and $R_2$ and $R_3$, together with the quaternized nitrogen atom, can form a heterocyclic radical containing from 1 to 2 heteroatoms selected from the group of nitrogen, sulfur and oxygen, in which case $R_1$ can represent a double bond in the heterocyclic structure or can be any of the aforementioned groups for $R_1$, $R_2$ and $R_3$; said groups $R_1$, $R_2$ and $R_3$ each having from 1 to 30 carbon atoms and at least one of $R_1$, $R_2$ and $R_3$ is a radical having from 8 to 30 carbon atoms when $R_2$ and $R_3$ are not part of a heterocyclic moiety; and $A^-$ is an anion derived from an oxylated sulfur compound, having the formula:

$$R'SO_3^-$$

wherein R' is alkyl, alkoxy, phenyl, phenoxy, alkylphenyl, alkylphenoxy, phenylalkyl or phenoxyalkyl and wherein the alkyl moieties of said R' groups contain from 1 to 20 carbon atoms and said R' groups are optionally alkoxylated with from 1 to 20 units of ethyleneoxide and/or propylene oxide. Representative of the above anions, $R'SO_3^-$, are methyl sulfate, methyl sulfonate, ethyl sulfate, ethyl sulfonate, (8)ethoxylated methyl sulfate, (6) propoxylated methyl sulfate, (10) propoxylated ethyl sulfate, (4)ethoxylated ethyl sulfonate, lauryl sulfate, (3)ethoxylated lauryl sulfate, lauryl sulfonate, decyl sulfate, dodecyl sulfonate, octadecyl sulfate, octadecyl sulfonate, tetradecyl sulfate, tetradecyl sulfonate, (4) ethoxylated lauryl sulfonate, $C_{12}$ to $C_{20}$ α-olefin sulfates and sulfonates or mixtures thereof, xylene sulfate, xylene sulfonate, benzene sulfate, benzene sulfonate, ethylphenyl sulfate, dodecylphenyl sulfonate, toluene sulfate, toluene sulfonate, etc. and mixtures thereof.

The compounds of the present invention can be prepared by several different methods. For example, sulfates and sulfonates corresponding to the above anions may be ion exchanged with the halides of the compounds disclosed in co-pending patent applications Ser. No. 922,923, filed October 24, 1986; Ser. No. 067,195, filed June 29, 1987; and Ser. Nos. 091,010; 091,008 and 091,149 all filed August 28, 1987 and all applications entitled QUATERNIZED NITROGEN CONTAINING COMPOUNDS and incorporated herein by reference. Said halide compounds are defined by the general formula

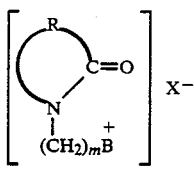

wherein $X^-$ is a chloride, bromide, or iodide anion; m is an integer having a value of from 1 to 4; R is alkylene having from 3 to 8 carbon atoms and is optionally substituted with $C_1$ to $C_4$ alkyl; $B^+$ is a quaternized nitrogen group selected from the group of A-D represented by the formulae:

 A.

wherein $R_1$, $R_2$ and $R_3$ are each independently selected from the group of alkyl, alkyl oxide, alkylhydroxy, alkoxy, aryl, aralkyl, alkaryl and alkyl amidoalkyl radicals, said groups each having from 1 to 30 carbon atoms and at least one of $R_1$, $R_2$ and $R_3$ being a radical having from 8 to 30 carbon atoms;

 B.

wherein $R_4$ forms a double bond in the heterocyclic ring with the quaternized nitrogen or is alkyl, alkyleneoxyalkyl, alkylhydroxy, aryl, aralkyl, aralkenyl, alkaryl and alkylamidoalkyl, said groups containing up to 30 carbon atoms; and $R_5$ together with the quaternary nitrogen atom forms a 5 to 10 membered monocyclic ring, a 9 to 10 membered bicyclic ring or a 13 to 14 membered tricyclic ring, at least one of said rings containing from 1 to 2 hetero atoms selected from the group of nitrogen, sulfur and oxygen and being saturated or unsaturated as may occur for example in the rings of thiazirine, N-methyl-thiazine, N-methyl-oxazine, thiazepine, N-ethyl-oxazocine, diazocine, N-methylazonine, antipyrine, conyrine, coniine, collidine, diazine, imidazole, isoxazole, lutidine, N-methyl hexahydropyridine, morpholine, oxazole, picoline, piperidine, pyrine, pyrazole, pyridine, pyrrolidine, pyrrole, pyrroline, N-ethylbenzopyrrole, N,N'-dimethyl-dipyrrylmethane, decahydroquinoline, methyl indole, nicotine, quinoline, quinaldine, acridine and carbazole. As indicated, a heterocyclic ring of the $R_5$ moiety may contain carbonyl substitution or the ring itself can be substituted with a lower alkyl, amino or amido group.

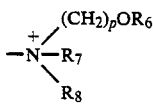 C.

wherein p is an integer having a value of from 2 to 4; $R_6$ is alkyl or alkenyl having from 1 to 30 carbon atoms; $R_7$ and $R_8$ are each independently selected from the group of $-(CH_2)_pOR_1$, alkyl, alkylhydroxy, aryl, aralkyl, aralkenyl, alkaryl and alkyl amidoalkyl radicals, said $R_7$ and $R_8$ groups having from 1 to 30 carbon atoms and at least one of $R_6$, $R_7$ and $R_8$ being a radical having from 8 to 30 carbon atoms; and

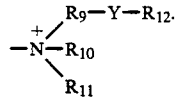 D wherein $R_9$ is alkylene having from 1 to 4 carbon atoms, phenyl or naphthyl optionally substituted with lower alkyl; Y is

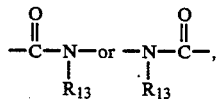

where $R_{13}$ is hydrogen or lower alkyl; $R_{12}$ is alkyl of from 1 to 30 carbon atoms; $R_{10}$ and $R_{11}$ are each independently selected from the group of $-R_9-Y-R_{12}$, alkyl, alkylene-oxyalkyl, alkylhydroxy, aryl, aralkyl, aralkenyl, alkaryl and alkyleneamidoalkyl radicals, said groups having from 1 to 30 carbon atoms and at least one of $R_{12}$, $R_{10}$ and $R_{11}$ being a radical having at least 8 carbon atoms.

The above nitrogen quaternized compounds and their preparations are described in detail in the above cited co-pending applications, which applications are incorporated herein by reference.

Sulfate and sulfonate reactant ion exchange agents which undergo ion exchange with the above halides include alkali metal and ammonium salts of the above sulfate and sulfonate anions and are defined by the formula

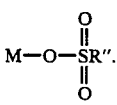 E wherein M is ammonium or an alkali metal and R'' is alkyl, alkoxy, aryl, aralkyl or alkaryl having from 1 to 20 carbon atoms optionally substituted with (1) to (20) units of ethyleneoxide and/or propyleneoxide or a $C_{12}$ to $C_{20}$ α-olefin or mixtures thereof.

Suitable species of this type include sodium methyl sulfate, sodium methyl sulfonate, lithium methyl sulfate, lithium methyl sulfonate, potassium ethyl sulfate, potassium ethyl sulfonate, (8)ethoxylated sodium methyl sulfate, (6)propoxylated sodium methyl sulfate, (10) propoxylated sodium ethyl sulfate, (4) ethoxylated potassium ethyl sulfonate, sodium lauryl sulfate, sodium lauryl sulfonate, potassium decyl sulfate, sodium dodecyl sulfonate, ammonium octadecyl sulfate, potassium octadecyl sulfonate, ammonium tetradecyl sulfate, sodium tetradecyl sulfonate, (4) ethoxylated lauryl sodium sulfonate, (4) ethoxylated lauryl sodium sulfate, sodium xylene sulfate, potassium xylene sulfonate, ammonium benzene sulfate, ammonium benzene sulfonate, ammonium ethylphenyl sulfate, sodium dodecylphenyl sulfonate, sodium toluene sulfate, sodium toluene sulfonate, sodium or ammonium $C_{12}$ to $C_{20}$ α-olefin sulfonates, etc. Of these the sodium or ammonium methyl or ethyl sulfates and sulfonates and sodium or ammonium toluene sulfates and sulfonates are preferred.

The ion exchange reaction involving the present anion exchange agents and the aforementioned quaternized halides, preferably the chlorides, can be effected directly when the anion of the anion exchange agent has a lower solubility than the halide, e.g. the chloride, of the quaternized halide compound. This method (Method 1) is carried out under mild conditions, for example between about room temperature and about 80° C. for a period of from about 10 minutes to about 4 hours, preferably between about 40° and about 65° C. for a period of from about 15 minutes to about 1 hour. The reactants are contacted in an aqueous solution in which the mole ratio of anion exchange agent to quaternized halide is between about 1:1 and about 1.5:1. The solid product which precipitates out of solution, is filtered and washed to remove alkali metal halide or ammonium halide by-product. Anion exchange agents having relatively low solubilities include sodium toluene sulfonate, sodium xylene sulfonate, etc.

The products of this invention can also be prepared by using an anion exchange resin (Method 2). In this case, the ion exchange is accomplished in a packed column with an ion exchange resin of the Amberlyte type which is a quaternized ammonium halide salt of a styrene-divinylbenzene copolymer having a macroreticular structure forming the matrix of said resin. An aqueous solution of the sulfate or sulfonate anion exchange agent is passed through the column to displace the halide and to replace the halide of the resin matrix with the corresponding sulfate or sulfonate anion. The quaternized halide is then passed through the column and exchanges its halide anion with the sulfate or sulfonate anion of the resin, thus regenerating the original ion exchange resin. This process is effected under ambient conditions with any of the alkali metal or ammonium sulfates or sulfonates described above.

The products of this invention can also be prepared by reactions involving a hydroxy alkyl lactam having the formula

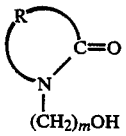

a tertiary amine and a suitable organo sulfonyl halide (Method 3).

In Method 3 the quaternized sulfonate salt of an alkyl lactam is formed in situ by reacting the hydroxy alkyl lactam with an organo sulfonyl halide in the presence of a tertiary amine having the formula

in a mole ratio of from about 1:2 to about 1:4 and an organo sulfonyl halide, preferably an organo sulfonyl chloride, e.g.

$R''SO_2Cl$      F.

wherein $R''$ is as defined above and is preferably methyl or tolyl.

The mole ratio of lactam to sulfate or sulfonate is employed between about 1:1 and about 1:0.9.

This reaction is carried out in a suitable inert solvent such as a haloalkane or aromatic liquid, e.g. methylene chloride, benzene, toluene, xylene and the reaction is run at solvent reflux for a period of from about 15 minutes to about 4 hours. The mole ratio of solvent to reactants is between about 1:1 and about 4:1. In this reaction the sulfonate of the hydroxy alkyl lactam forms in situ and then reacts with the tertiary amine.

Finally, the present products can be prepared by Method 4 which comprises reacting the above hydroxyalkyl lactam with a secondary amine to produce the corresponding tertiary amine intermediate and then quaternizing the tertiary amine with sulfate or sulfonate of formula $R''SO_2OR'''$      G.

wherein $R''$ is as defined above and $R'''$ is a radical having from 1 to 20 carbon atoms, optionally substituted with (1) to (20) $C_2$ to $C_3$ alkyleneoxide units and is selected from the group of a $C_{12}$ to $C_{20}$ α-olefin or mixtures thereof, alkyl, aryl, alkaryl or aralkyl. Of these organo sulfates and sulfonates, those ethoxylated and non-alkoxylated compounds wherein $R'''$ alkyl or tolyl and $R''$ is methyl, methoxy, ethyl, ethoxy, tolyl or tolyloxy are preferred.

The mole ratio of secondary amine having the formula

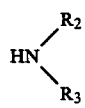

to lactam can vary between about 1:1 and about 1:2 and the mole ratio of lactam to quaternizing agent is about 1:1. This reaction is also conducted in the presene of an inert solvent such as those recited for Method 3 and is effected at a temperature above the melting point of the amine up to about 130° C. for a period of from about 1 to about 3 hours.

Most preferred quaternizing agents for the reactions involving the hydroxyalkyl lactams include dimethyl sulfate or sulfonate, diethyl sulfate, methyl toluene sulfate or sulfonate, octadecyl methane sulfonate, dodecylmethane sulfonate and lauryl (3)ethoxymethane sulfonate.

The preferred products of the reactions involving the hydroxy alkyl lactams are generally defined by the formula

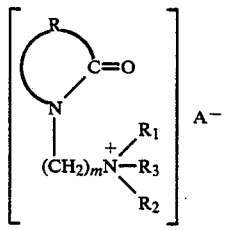

wherein $R_1$ is a $C_{14}$ to $C_{18}$ alkyl and $R_2$ and $R_3$ are each lower alkyl.

The sulfate and sulfonate quaternized products of this invention show greatly increased heat stability with no product breakdown for the period tested, i.e. 1 month at 50° C. Accordingly, they are particularly suited for formulations normally stored for long periods or at elevated temperatures as encountered in warehouses, etc. They serve as excellent fabric softeners for use in clothes dryers and their antistatic properties make them useful in plastic processing and machining to dissipate charge build up. Conditioning properties and non-toxicity of the present compounds renders them ideally suitable as additives in cosmetic applications, e.g. in hair and skin treating creams, lotions or gels. Particular benefit is derived from their incorporation in shampoos, mousses and in clear conditioners. When employed in commercial formulations of the above type, they may be employed in a concentration of between about 0.001 wt. % and about 30 wt. % based on total composition.

Having thus described the invention, reference is now had to the examples which illustrate preferred embodiments but which are not to be construed as limiting to the scope of the invention as more broadly described above and in the appended claims.

EXAMPLE 1

Preparation of octadecyldimethyl N-[(2-pyrrolidonyl) methyl]ammonium tosylate ($SO_3$—$C_6H_4$—$CH_3$)

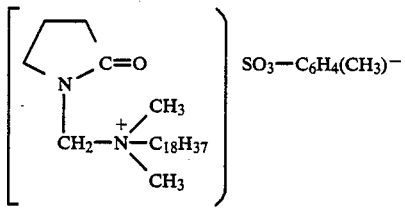

by solubility exchange of quaternaries.

To a flask equipped with stirrer and thermometer was added at ambient temperature 50.0 g. distilled water 7.2 g. sodium hydroxide solution (50%) and 13.3 g. (0.069 m) p-toluenesulfonic acid monohydrate, [$C_6H_4(CH_3)$-$SO_3H$]. The mixture was stirred at ambient temperature for about 0.5 hour, after which 30.0 g. (0.069 m) octadecyldimethyl N-[(2-pyrrolidonyl) methyl]ammonium chloride was added. The reaction mixture was heated to 40°–45° to ensure complete solution and stirring continued for an additional 2 hours. The reaction was then cooled to 10°–15° C. to precipitate the crude tosylate salt product. The crude product was filtered to recover 19.8 g. of white solid product, which product was found to have 98.2% quaternized product, 0.4% amine, and 0.04% chloride. The above solid was heated in a 50° oven for 30 days and showed no loss of activity.

EXAMPLE 2

Preparation by Ion Exchange Resin

To a glass chromatography column was charged 450 g. Amberlyte IRA 900 ion exchange resin*. The column was washed with one liter of methanol followed by one liter of distilled water.

* a macroreticular strongly anion exchange resin having a halide attached to the resin matrix of styrene/divinylbenzene A solution of sodium tosylate, prepared by addition of 332.9 g. p-toluenesulfonic acid monohydrate to 1720 g. water followed by neutralization with 140 g. of 50% sodium hydroxide, was then passed through the packed column at a rate sufficient to permit displacement of the Amberlyte halide and to replace it with toluene sulfonate. The column was then washed with one 1 liter of methanol. A solution of 153 g. dimethyloctadecyl[2-(pyrrolidonyl) methyl]ammonium chloride (98.4% pure) in 500 ml methanol was passed through at a rate sufficient to exchange the chloride of the lactam with the toluene sulfonate of the resin. The column was then washed with 500 ml methanol and the methanol evaporated leaving 200 g. of 98% pure quaternized product. The product showed no loss of activity after storage at 50°C. for 60 days.

EXAMPLE 3

Preparation of Dimethyloctadecyl [(2-azacycloheptanyl)methyl]ammonium chloride starting material

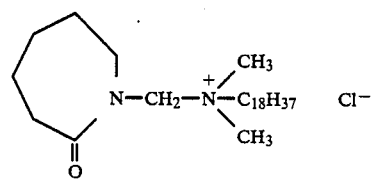

To a flask equipped with a stirrer and thermometer was added 575 g. ethyl acetate and 93.3 g. (0.3 m) dimethyloctadecylamine. Nitrogen was slowly bubbled through the reactor after which 50.0 g. (0.3 m) chloromethylcaprolactam was gradually added over a 15 minute period. The solution exothermed to 50° and was held at 50° for 1 hour. The reaction mixture was then cooled to 10°-15° C., filtered, washed 2 times with cold ethyl acetate and dried under high vacuum yielding 126.5 g. (89.5% of Theory) of the white solid product. Analysis showed 87% quaternized product and 12% amine + amine HCl.

The product of this example is substituted for dimethyloctadecyl [(b 2-pyrrolidonyl)methyl]ammonium chloride in Example 2 and the resulting dimethyloctadecyl N-[(2-aza cycloheptanoyl) methyl]ammonium toluene sulfonate was recovered. This quaternized product maintains its activity when stored at 50° C. for one month.

EXAMPLE 4

Example 2 was repeated except that sodium methyl sulfonate was substituted for sodium toluene sulfonate. The resulting quaternized product, dimethyloctadecyl N-[(2-pyrrolidonyl)methyl]ammonium methylsulfonate, (94.3% pure quaternized compound) was recovered. This product showed only 1% loss of activity when stored at 50° C., for 60 days.

EXAMPLE 4A

The same result as reported in Example 4 was achieved when sodium methosulfate was substituted for sodium toluene sulfonate. The methosulfate (96.7% pure quaternized compound) lost only 2% activity after 30 days storage at 50° C.

EXAMPLE 5

Preparation of dimethyl octadecyl [(2-piperidonyl) methyl)]ammonium chloride starting material

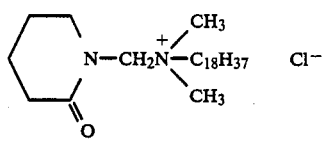

To a flask equipped with a mechanical stirrer and a thermometer was added 490 g. ethyl acetate and 82.2 g. (0.28 m) dimethyloctadecylamine. Nitrogen was slowly bubbled through the solution after which 40.0 g. (0.27 m) chloromethylvalerolactam was added over a 5 min. period.

The solution exothermed to 45° C. and was held at that temperature for 1 hour. The mixture was then cooled to 10° C. and stirred for 1 hour to precipitate the quaternized chloride product. The product was filtered, washed twice with 100 ml ethyl acetate and dried in a desicator for 8 hours at 37° C. under high vacuum. The reaction yielded 108.6 g. (90% of Theory) of white solid, 87.1% quaternized chloride containing, 12.3% amine + amine HCl.

EXAMPLE 6

Preparation of dimethyl octadecyl [(2-piperidonyl)methyl] ammonium methosulfonate

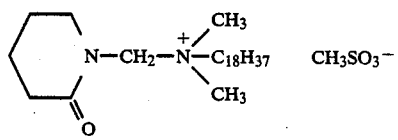

The chloride of Example 5 was converted to the methanesulfonate by ion exchange using Amberlyte 1R900 by procedure as described in Example 4. This product, like those above, showed good heat stability at 50° C. for a period of at least one month.

EXAMPLE 7

Syntheses of Dimethyloctadecyl Pyrrolidonyl Methyl Ammonium p-toluenesulfonate Product from Hydroxymethyl Lactam To a 1 liter round bottom flask was added 28.8 g. (0.250 moles) of hydroxymethyl-2-pyrrolidone, 163 g. (0.550 moles) of dimethyloctadecylamine and 200 ml of methylene chloride. The flask was equipped with a mechanical stirrer, reflux condenser, thermometer, dropping funnel and drying tube. A solution of 52.4 g. (0.275 moles) of p-toluenesulfonyl chloride in 200 ml of methylene chloride was slowly introduced into the reaction flask at 25°-28° C. The reaction flask was heated to reflux for 1 hour. The resulting hot slurry was transferred to a 1 liter one neck flask and the solvent was stripped by a rotoevaporator. The quaternized product collected weighed 241 g. and was analyzed as 54.7% quaternized tosylate and 42.6% amine hydrochloride. This translates to a 93.2% conversion of hydroxymethyl-2-pyrrolidone to the quaternary product.

The above mixture can be purified to 90% active quaternary product by neutralization of the amine hydrochloride with potassium hydroxide and hexane extraction of the free amine. Other bases can be used for neutralization, e.g., potassium carbonate, sodium hydroxide.

The product of this reaction showed the same high temperature stability as that of Example 2.

EXAMPLE 8

Preparation of N-pyrrolidonylmethyl Di(dihydrogenated tallow) Amine Starting Material

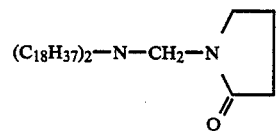

To a 500 ml round bottom flask equipped with Dean Starke tube stirrer and thermometer was charged 50.0 g. (0.1 m) dihydrogenated tallow amine (Armeen 2HT), 11.65 g. (0.1 m) hydroxymethylpyrrolidone and 150 ml toluene. The reaction mixture is heated to reflux. Water of reaction is removed via the Dean Starke apparatus over a period of 1.5 hours. A total of 1.75 ml (TH = 1.8 ml) of water was collected. Toluene was removed by heating to 100° under house vacuum (23") and then under high vacuum (1 to 2 mm of Hg). The product, yield 56.6 g. (95% of Theory) was recovered and analyzed. Analysis by titration indicated 8% secondary 87% tertiary amine.

The reaction conditions were determined by azeotrope solvent. It is to be understood that other solvents can be used in the reaction, e.g. benzene, xylene, etc.

EXAMPLE 9

Preparation of Pyrrolidonylmethyl Di(dihydrogenated tallow) Ethyl Ammonium Ethosulfate

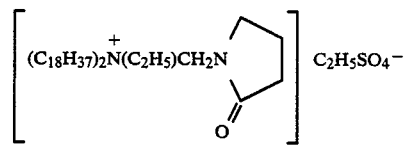

To a 100 ml round bottom flask equipped with thermometer, stirrer and condenser was added 36.4 g. (0.06 m) of the pyrrolidonylmethyl di(dihydrogenated tallow) amine of Example 8 and 9.3 g. (0.06 m) diethylsulfate. The reaction mixture was heated to 100°C. and held at that temperature for 1 hour. The reaction mixture was then heated to 130° C. and held 2 hours. Cooling yielded 42 g. (93% of Theory) of quaternized ethyl sulfate salt. Analysis by tetraphenylboron method indicated 85% purity.

The product of this example showed good heat stability at 50° C. for at least one month.

EXAMPLE 10

Preparation of octadecyldimethyl [3-(2-pyrrolidonyl)propyl]ammonium tosylate according to

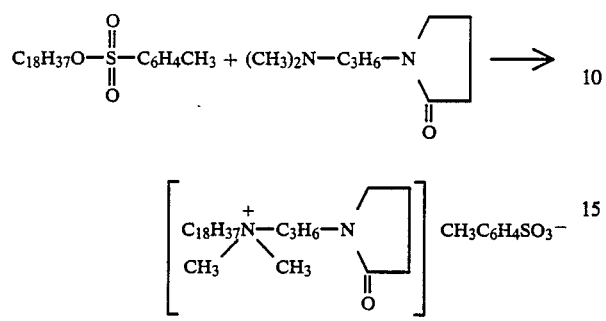

To a 100 ml round bottom flask equipped with a thermometer and stirrer containing 167 g. of propylene glycol was added 50.7 g. of octadecyl-p-toluenesulfonate and 20.9 g. of [(dimethylamino)propyl]-2-pyrrolidone. The mixture was heated to 100° C. and stirred at that temperature for 6 hours after which it was cooled and recovered. Analysis by quaternary tetraphenyl boron indicated 22% activity corresponding to a 74% conversion.

EXAMPLE 11

Heat Stability of Quaternaries

The compounds as well as aqueous solutions of the compounds described in the preceding Examples were heated to 50° C. in an oven for extended periods of time. Results are summarized.

| Compound | % Activity Zero time | % Activity 30 days at 50° | % Activity 60 days at 50° |
|---|---|---|---|
| Example 1 | 93.2 | 94.9 | 95.3 |
| 20% aq. Ex. 1 | 19.1 | 19.2 | 18.9 |
| Example 4 | 94.3 | 92.5 | 89.5 |
| 40% aq. Ex. 4 | 41.6 | 41.7 | 40.3 |
| Example 4A | 96.6 | 93.7 | — |
| 20% aq. Ex. 4A | 19.23 | — | 19.00 |

EXAMPLE 12

Quaternaries as Softeners

Terry cotton swatches were padded with approximately 0.6% aqueous solution of the surfactants to be tested to provide about 0.1% active addition. The swatches were hang dried for 24 hours and their softness evaluated by a paired comparison. Results showed that compounds of Examples 1, 4 and 4A were equivalent or better than distearyldimethylammonium methosulfate, and were far superior in the softness than untreated control swatches.

EXAMPLE 13

The following formulation is representative of a hair shampoo which incorporates a heat stable quaternized lactam of this invention for hair conditioning, namely softness, combability, improved texture and body.

| Ingredient | % by Wt. |
|---|---|
| $C_{14}$-$C_{16}$ Alpha Olefin Sulfonate Mixture | 15.00 |
| Ammonium Lauryl Sulfate | 20.00 |
| Compound of Example 1 | 10.00 |
| Cocamidopropyl Betaine | 3.50 |
| N—dodecyl-2-pyrrolidone | 1.00 |
| Sodium Laureth-4-Phosphate | 1.00 |
| Hydrolyzed Animal Protein | 0.25 |
| Tetrasodium ethylene diamine tetra acetic acid | 0.15 |
| Deionized water | Q.S. |
| Fragrance | Q.S. |
| Preservative (Kathon CG)* | Q.S |

*5-chloro-2-methyl-4-isothiazolin-3-one (Rohm & Haas)

EXAMPLE 14

Representative of other cosmetic uses of the present quaternized lactams of this invention are the following skin conditioning formulation and body shampoo.

| SKIN LOTION | |
|---|---|
| Ingredient | % by Wt. |
| Stearic Acid | 3.00 |
| Mineral Oil, 70 cts | 2.00 |
| Emulsifying Wax | 3.00 |
| Dimethicone | 1.50 |
| Deionized Water | Q.S. |
| Carbomer 934* | 0.15 |
| Oleth-20** | 1.00 |
| Compound of Example 9 | 1.00 |
| Triethanolamine, 98% | 1.00 |
| Preservative | Q.S. |
| Fragrance | Q.S. |

*a crosslinked polymer of acrylic acid (B. F. Goodrich)
**the polyethylene glycol ether of oleyl alcohol (GAF Corp.)

| BODY SHAMPOO | |
|---|---|
| Ingredient | % by Wt. |
| Deionized water | Q.S. |
| $C_{14}$-$C_{16}$ Alpha Olefin Sulfonate | 35.00 |
| Sodium Methyl Cocyl Taurate | 12.00 |
| Polyethylene glycol-150 Distearate | 1.00 |
| Glycol Distearate | 2.00 |
| Quaternized product of Example 3 | 6.00 |
| Polyquaternium-11 | 2.50 |
| Cocamidopropyl Betaine | 10.00 |
| Citric Acid | to pH 6.0 |
| Fragrance | Q.S. |
| Preservative (Kathon CG) | Q.S. |

What is claimed is:

1. A quaternized lactam having the formula:

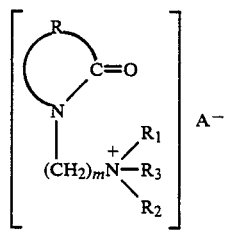

wherein m is an integer having a value of from 1 to 4; R is alkylene having from 3 to 8 carbon atoms and is optionally substituted with $C_1$ to $C_4$ alkyl; $R_1$, $R_2$ and $R_3$ are each independently selected from the group of alkyl, alkyloxyalkyl, alkyloxyalkenyl, hydroxyalkyl, aryl, aralkyl, alkaryl, alkyl amidoalkyl, alkyl carbamoylalkyl, aryl amido alkyl and aryl carbamoylalkyl radicals, and R₂ and R₃, together with the quaternized nitrogen atom can form a saturated or unsaturated 5 to 10 membered monocyclic ring; a 9 to 10 membered bicyclic ring or a 13 to 14 membered tricyclic ring, which rings may contain a carbonyl group and which rings are optionally substituted with lower alkyl, amino or amido, at least one of said rings containing from 1 to 2 heteroatoms selected from the group of nitrogen, sulfur and oxygen, and, where the quaternized nitrogen atom in the heterocyclic structure is doubly bonded to an adjacent ring atom, R₁ represents one bond of said double bond in the heterocyclic structure, otherwise R₁ bonded to the quaternized nitrogen in a heterocyclic structure is any of the aforementioned individual groups for R₁, R₂ and R₃; said groups R₁, R₂ and R₃ each having from 1 to 30 carbon atoms and at least one of R₁, R₂ and R₃ is a radical having from 8 to 30 carbon atoms when R₂ and R₃ are not part of a heterocyclic moiety; and A⁻ *is an anion derived from an oxylated sulfur compound, having the formula:*

R'SO₃⁻ wherein R' is alkyl, alkoxy, phenyl, phenoxy, alkylphenyl, alkylphenoxy, phenylalkyl, phenoxyalkyl, C₁₂ to C₂₀ α-olefin or mixtures thereof and wherein the alkyl moieties of said R' groups contain from 1 to 20 carbon atoms and said R' groups are optionally alkoxylated with from 1 to 20 units of ethyleneoxide and/or propylene oxide.

2. The lactam of claim 1 wherein m has a value of 3 and R is alkylene of from 3 to 6 carbon atoms.

3. The lactam of claim 1 wherein R' is selected from the group of alkyl, alkoxy, methylphenyl and methylphenoxy.

4. The lactam of claim 1 wherein R₁, R₂ and R₃ are hydrocarbon radicals.

5. The lactam of claim 4 wherein R is alkylene of from 3 to 6 carbon atoms, m has a value of one and R' is selected from the group of alkyl, alkoxy, methylphenyl and methylphenoxy.

6. The process of adding a sufficient conditioning and heat stabilized amount of the compound of claim 1 to a cosmetic formulation.

7. The process of claim 6 wherein said formulation is a shampoo.

8. The process of claim 6 wherein said formulation is a skin lotion.

9. The process of contacting of fabric with a sufficient softening heat stabilized amount of the compound of claim 1 during a laundering operation.

10. The process of claim 9 wherein said laundering operation is a cloths drying operation.

11. The process of claim 9 wherein said laundering operation is a washing operation.

12. The process for synthesizing the lactam of claim 1 which comprises forming an aqueous solution of a quaternized lactam having the formula:

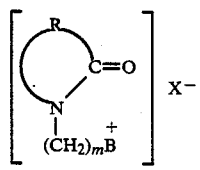

wherein X⁻ is a chloride, bromide, or iodide anion; m is an integer having a value of from 1 to 4; R is alkylene having from 3 to 8 carbon atoms and is optionally substituted with C₁ to C₄ alkyl; B⁺ is a quaternized nitrogen group selected from the group of A-D represented by the formulae:

 A.

wherein R₁, R₂ and R₃ are each independently selected from the group of alkyl, alkyl oxide, alkylhydroxy, alkoxy, aryl, aralkyl, alkaryl and alkyl amidoalkyl radicals, said groups each having from 1 to 30 carbon atoms and at least one of R₁, R₂ and R₃ being a radical having from 8 to 30 carbon atoms;

 B.

wherein [R₄ forms a double bond in the heterocyclic ring with the quaternized nitrogen or is alkyl, alkyleneoxyalkyl, alkylhydroxy, aryl, aralkyl, aralkenyl, alkaryl and alkylamidoalkyl, said groups containing up to 30 carbon atoms; and] R₅ together with the quaternary nitrogen atom forms a saturated or unsaturated 5 to 10 membered monocyclic ring, a 9 to 10 membered bicyclic ring or a 13 to 14 membered tricyclic ring, at least one of said rings containing from 1 to 2 hetero atoms selected from the group of nitrogen, sulfur and oxygen and the heterocyclic ring of the R₅ moiety may contain a carbonyl group or the ring itself can be substituted with a lower alkyl, aminio or amido group and, where the quaternized nitrogen atom in the heterocyclic structure is doubly bonded to an adjacent ring atom, R₄ represents one bond of said double bond, otherwise R₄ is alkyl, alkyleneoxyalkyl, alkylhydroxy, aryl, aralkyl, aralkenyl, alkaryl and alkylamidoalkyl, said groups containing up to 30 carbon atoms;

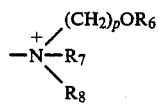 C.

wherein p is an integer having a value of from 2 to 4; R₆ is alkyl or alkenyl having from 1 to 30 carbon atoms; R₇ and R₈ are each independently selected from the group of —(CH₂) ₚOR₁, alkyl, alkylhydroxy, aryl, aralkyl, aralkenyl, alkaryl and alkyl amidoalkyl radicals, said R₇ and R₈ groups having from 1 to 30 carbon atoms and at least one of R₆, R₇ and R₈ being a radical having from 8 to 30 carbon atoms; and

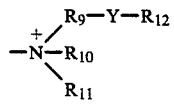 R wherein R₉ is alkylene having from 1 to 4 carbon atoms, phenyl or naphthyl optionally substituted with lower alkyl; Y is

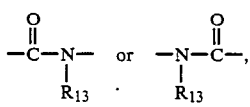

where $R_{13}$ is hydrogen or lower alkyl; $R_{12}$ is alkyl of from 1 to 30 carbon atoms; $R_{10}$ and $R_{11}$ are each independently selected from the group of $-R_9-Y-R_{12}$, alkyl, alkylene-oxyalkyl, alkylhydroxy, aryl, aralkyl, aralkenyl, alkaryl and alkyleneamidoalkyl radicals, said groups having from 1 to 30 carbon atoms and at least one of $R_{12}$, $R_{10}$ and $R_{11}$ being a radical having at least 8 carbon atoms; and contacting said aqueous solution with a quaternizing agent in a mole ratio of from about 1:1 and about 1:1.5 at between about room temperature and about 80° C. for a period of from about 10 minutes to about 4 hours, said quaternizing agent having the formula

wherein M is ammonium or an alkali metal and R" is a radical having 1 to 20 carbon atoms selected from the group consisting of $C_{12}$ to $C_{20}$ α-olefins, alkyl, alkoxy, aryl, aryloxy, alkaryl, alkaryloxy, aralkyl and aralkoxy which groups are optionally substituted with from 1 to 20 units of $C_2$ to $C_3$ alkyleneoxide and mixtures thereof.

13. The process of claim 12 wherein the water solubility of the quaternizing agent is less than the halide of the lactam and wherein the reaction is carried out in solution.

14. The process of claim 12 wherein a granular styrene-divinylbenzene halide resin in a packed column is anion exchanged with said quaternizing agent and wherein said aqueous solution of said quaternized lactam halide is thereafter passed through said packed column for anion exchange with said resin.

15. The process for synthesizing the lactam of claim 1 which comprises reacting a mixture of components consisting essentially of an N-alkylhydroxide lactam having the formula

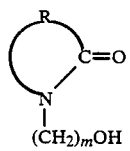

with an amine having the formula

and a quaternizing agent having the formula

wherein R, $R_2$, $R_3$, R" and m are as defined, $R_4$ is hydrogen or $R_l$ and '" is a halide or a radical having from 1 to 20 carbon atoms selected from the group of $C_{12}$ to $C_{14}$ α-olefins, alkyl, aryl, alkoxy, aryloxy, alkaryloxy and aralkyloxy wherein said mixture of components is contacted under ambient conditions in an inert solvent where the mole ratio of solvent to total reactants is between about 1:1 and about 1:4, the mole ratio of N-alkylhydroxy lactam to amine is between about 1:4 and about 2:1 and the mole ratio of lactam to quaternizing agent is between about 1:1 and about 1:1.5.

16. The process of claim 15 wherein the amine is a tertiary amine, R" of the quaternizing agent is alkyl, the sulfonate of the lactam forms in situ as an intermediate and said sulfonate reacts with said tertiary amine to produce the quaternized product of the process.

17. The process of claim 15 wherein the amine is a secondary amine, R" of the quaternizing agent is alkyl, the tertiary amine of the lactam forms in situ as an intermediate and said quaternizing agent reacts with said tertiary amine to produce the quaternized product of the process 18. An aqueous composition containing between about 0.001 and about 30 wt. % of the quaternized lactam of claim 1.

19. The composition of claim 18 wherein said composition is a conditioner in a cosmetic formulation.

20. The composition of claim 18 wherein said composition is a conditioning softening agent in a laundering formulation.

* * * * *